(12) United States Patent
Link

(10) Patent No.: US 7,947,084 B2
(45) Date of Patent: May 24, 2011

(54) HIP JOINT PROSTHESIS WITH A SHAFT TO BE INSERTED INTO THE FEMUR

(75) Inventor: Helmut D. Link, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 465 days.

(21) Appl. No.: 11/659,346

(22) PCT Filed: Aug. 5, 2005

(86) PCT No.: PCT/EP2005/008513
§ 371 (c)(1),
(2), (4) Date: Feb. 5, 2007

(87) PCT Pub. No.: WO2006/015812
PCT Pub. Date: Feb. 16, 2006

(65) Prior Publication Data
US 2008/0033568 A1 Feb. 7, 2008

(30) Foreign Application Priority Data
Aug. 6, 2004 (EP) .................... 04018714

(51) Int. Cl.
*A61F 2/32* (2006.01)
(52) U.S. Cl. .................... 623/23.26; 623/23.3
(58) Field of Classification Search ..... 623/23.15–23.46
See application file for complete search history.

(56) References Cited

U.S. PATENT DOCUMENTS

| 3,995,323 | A | 12/1976 | Shersher |
| 4,718,915 | A | 1/1988 | Epinette |
| 5,370,698 | A | 12/1994 | Heimke et al. |
| 5,755,811 | A | 5/1998 | Tanamal et al. |
| 5,947,893 | A * | 9/1999 | Agrawal et al. ............... 600/36 |
| 6,296,667 | B1 | 10/2001 | Johnson et al. |
| 6,695,884 | B1 * | 2/2004 | Townley ................. 623/23.26 |
| 7,175,668 | B2 * | 2/2007 | Zweymuller ............. 623/23.24 |
| 7,494,510 | B2 * | 2/2009 | Zweymuller ............. 623/23.35 |
| 2002/0049497 | A1 | 4/2002 | Mason |
| 2002/0127261 | A1 | 9/2002 | Risbud et al. |
| 2005/0240272 | A1 * | 10/2005 | Zubok et al. .............. 623/17.15 |

FOREIGN PATENT DOCUMENTS

| AT | 391264 | * 3/1990 |
| DE | 19 43 598 B2 | 3/1971 |
| DE | B-1943 598 | 3/1971 |
| DE | 195 08 753 A1 | 12/1995 |

(Continued)

OTHER PUBLICATIONS

Written Opinion, directed to counterpart application No. PCT/EP2005/008513 (5 pages).

(Continued)

*Primary Examiner* — Bruce E Snow
(74) *Attorney, Agent, or Firm* — Morrison & Foerster LLP

(57) ABSTRACT

A hip-joint prosthesis includes a shaft which is configured to be inserted into the femur and whose surface has an osteoinductive finish. This finish is provided exclusively in the metaphyseal portion of the shaft and laterally from the line delineating the maximum antero-posterior dimension of the shaft cross section. This ensures a better involvement of the metaphyseal spongiosa in the flow of forces, without compromising the ability to perform follow-up surgery on the prosthesis.

7 Claims, 2 Drawing Sheets

FOREIGN PATENT DOCUMENTS

| | | |
|---|---|---|
| EP | 0 093 230 B1 | 2/1983 |
| EP | 0 095 440 A1 | 5/1983 |
| EP | 0 128 036 A1 | 12/1984 |
| EP | 0 222 236 A1 | 10/1986 |
| EP | 0 478 532 A1 | 9/1991 |
| EP | 0 601 223 B1 | 6/1994 |
| EP | 0 761 182 A2 | 3/1997 |
| EP | 1 044 665 A2 | 10/2000 |
| FR | 2194123 | 2/1974 |
| FR | C-2.194.123 | 2/1974 |
| FR | 2356465 | 1/1978 |
| FR | A-2 356 465 | 1/1978 |
| GB | 1030145 | 5/1966 |
| WO | WO 93/08771 | 5/1993 |
| WO | WO-2004/069102 A1 | 8/2004 |
| WO | WO 2004/069102 A1 | 8/2004 |

OTHER PUBLICATIONS

T. Albrektsson et al. (1980). "Osteoinduction, Osteoconduction and Osseointegration," *General Principles*: 12-17.

Denissen H. et al. (1994). "Ceramic Hydroxyapatite Implants for the Release of Bisphosphonate," *Bone and Mineral* 25:123-134.

Yoshinari M. et al. (2002). "Bone Response To Calcium Phosphate-Coated and Bisphosphonate-Immobilized Titanium Implants," *Biomaterials*: 2879-2885.

Yoshinari M. et al. (2001). "Immobilization of Bisphosphonates On Surface Modified Titanium," *Biomaterials* 22:709-715.

(1992). "Farbatlanten Der Medizin (Colour Atlas of Medicine)," vol. 7: Locomotor Apparatus I, *Thieme Verlag Stuttgart*.

* cited by examiner

HIP JOINT PROSTHESIS WITH A SHAFT TO BE INSERTED INTO THE FEMUR

REFERENCE TO RELATED APPLICATIONS

This application is a national stage application under 35 USC 371 of International Application No. PCT/EP2005/008513, filed Aug. 5, 2005, which claims priority from European Application No. 04 018 714.8, filed Aug. 6, 2004, the entire contents of which are incorporated herein by reference.

FIELD AND BACKGROUND OF THE INVENTION

The spongy bone tissue in the metaphysis of the femur includes a complicated structure of bone trabeculae via which the parts of the bone subjected to compression loads and tensile loads at the femoral neck, the greater trochanter, the lesser trochanter and the diaphysis are connected in a manner transmitting compression and tension. In their totality, they form continuous tension and compression trajectories (Farbatlanten der Medizin [Colour Atlas of Medicine], Volume 7: Locomotor apparatus I., published by Thieme Verlag, Stuttgart, 1992). When the shaft of a hip-joint prosthesis is inserted, the primary tension trajectories in particular, which connect the femoral neck to the opposite intertrochanteric surface area of the bone, are for the most part interrupted. When they subsequently are no longer involved in the transmission of forces, they regress. This applies in particular when using prostheses whose prosthesis shaft is clamped in the diaphysis and in which the proximal, metaphyseal area of the femur, especially in its lateral part, is barely involved in force transmission. Attempts have been made, using what are called tension anchors, to connect the prosthesis shaft to the area of the greater trochanter and in this way to involve the latter in the flow of forces. A rod connected to the prosthesis shaft was guided through the greater trochanter and provided on the outside with a locking nut so that, upon loading of the hip prosthesis, a tension is exerted on the greater trochanter (U.S. Pat. No. 3,995,323, EP-B-93230, DE-B-1943598). However, it has been found that, because of the constant alternating loading, mechanical tension anchors of this kind quickly come loose and therefore are effective only for a short time. It is also known to design the shaft, or a wing projecting laterally therefrom into the area of the greater trochanter, in such a way that an intimate connection is obtained with the bone substance growing into pores or openings of this wing (GB-A-1030145, FR-A-2356465, EP-A-128036, EP-A-222236, EP-A-95440, EP-B-601223, EP-A-1044665, U.S. Pat. No. 5,755,811, U.S. Pat. No. 4,718,915, U.S. Pat. No. 5,370,698, FR-C-2194123). To promote connection of the bone to the prosthesis surface, it is also known to make the prosthesis surface osteoconductive. This term denotes surfaces which tolerate adjacent bone growth. These include surfaces made of titanium alloys and coatings which contain calcium phosphate or hydroxyapatite (EP-A-761182, WO 9308771).

More recently, substances have been made known which not only tolerate bone growth like the osteoconductive surfaces, but stimulate undifferentiated pluripotent stem cells for conversion to bone cells (Albrechtsson, Johansson: Osteoinduction, Osteoconduction and Osseointegration, in: Gunzburg Press: The use of bone substitutes in spine surgery; Springer. Denissen, H. et al.: Ceramic hydroxyapatite implants for the release of bisphosphonate, in: Bone and Mineral 1994, pages 123-134. Yoshinari, M. et al.: Bone response to calcium phosphate-coated and bisphosphonate-immobilized titanium implants, in: Biomaterials 2002, pages 2879-2885. Yoshinari, M. et al.: Immobilization of bisphosphonates on surface-modified titanium, in: Biomaterials 2001, pages 709-715). These substances include bisphosphonates and bone morphogenic proteins (BMP). These can also be used to finish the surfaces of bone prostheses, including hip prostheses (US-A-2002/0049497, US-A-2002/0127261). They lead to a very intimate connection of the prosthesis surface with the bone, which may be undesirable in the event of follow-up surgery because removal of the prosthesis from the bone may be impeded by this. This applies in particular when the shaft of a hip prosthesis is equipped in its entirety or to a substantial extent with such a substance (EP-A-478532, U.S. Pat. No. 6,296,667, DE-A-19508753).

SUMMARY OF THE INVENTION

The object of the invention is to improve the fixing of a femoral hip prosthesis in the bone without compromising the ability to perform follow-up surgery. The solution according to the invention lies in the features of the invention as disclosed herein.

Accordingly, in a hip-joint prosthesis with a shaft to be inserted into the femur, the osteoinductive coating is provided exclusively in a part of the shaft situated laterally from the line of maximum AP (antero-posterior) dimension in the metaphyseal portion.

In an earlier patent application (PCT/EP03/05292) not belonging to the published prior art, it was proposed that the finish with the osteoinductive substance be provided exclusively in the trochanteric area, which is defined as follows. Starting from the point of intersection between the centre line of the femoral neck and the centre line of the proximal end of the diaphysis, the trochanteric area lies laterally from the tangent drawn from this point of intersection to the top edge of the head of the hip, and laterally from the part of the centre line of the femoral neck that continues this tangent.

According to the present invention, the demarcation of the surface area to be finished with the osteoinductive substance is differently defined. The definition according to the invention is that the osteoinductive finish of the prosthesis surface is provided in that part of the metaphyseal portion in which there are particularly many surface areas whose directional normal contains a lateral component. Earlier experience has shown that, in these surface areas, there can be no expectation of a connection to the bone permitting transmission of tensile forces. By virtue of the osteoinductive coating, however, such a connection is made possible for the most part. The earlier application proposes the opposite, namely arranging the coating on surface areas which are undercut in relation to the lateral direction, i.e. pointing in the medial direction.

It is particularly expedient for the substance to be incorporated into a coating, which is also intended to be porous. The coating can be of any desired type. For example, it can be a porous metal layer. Coatings of particular advantage are ones which are originally osteoconductive and, for example, consist of calcium phosphate or hydroxyapatite.

The effect of the invention is that, very quickly after the operation, bone cells develop in immediate proximity to and in connection to the prosthesis surface. The result of this is that relative movements between the bone surface and the bone do not initially cause formation of a gap or an intermediate connective tissue layer which makes subsequent intimate connection more difficult or impossible. By virtue of the invention, there is a more rapid accumulation of bone on the trochanteric surface of the prosthesis and more rapid incorporation of bone into the pores and recesses thereof, so that the trochanteric area of the bone quickly achieves a permanent connection to the prosthesis and, as a result of this, is involved in the transmission of forces. By contrast, on the other surface areas, the connection to the bone is achieved only to the previously expected extent. Outside the trochanteric area, which is readily accessible in the event of follow-up surgery and therefore does not cause any problems even when the bone is very strongly bound, the physician, when performing follow-up surgery, therefore finds exactly those conditions with which he is already accustomed.

The part of the surface containing the osteoinductive substance expediently comprises pores or undercuts in relation to the lateral direction, so that the bone substance formed as a result of the osteoinduction can not only adhere to the surface but can also anchor onto it with a form fit.

In the middle of the trochanteric part of the bone, the spongy substance is sometimes less dense than it is near the cortex. For this reason, those portions of the osteoinductively finished surface areas of the prosthesis that point in the ventral and dorsal directions are preferably situated at a certain distance from the mid-plane of the bone and nearer the cortex. Therefore, the part of the prosthesis forming these surface areas ought not to be too thin in the AP direction. Its thickness, and thus the distance between said dorsal and ventral surface areas, is expediently over 6 mm, and more advantageously over 9 mm to approximately 15 mm.

The growth of fresh bone cells onto the prosthesis surface can be promoted by a press-fit of the surface areas in question. It is therefore expedient if the surfaces in question, and their mating surfaces, are made wedge-shaped in the direction in which the prosthesis is inserted into the bone, and if the rasp assigned to the prosthesis, and used to shape the receiving space for the prosthesis shaft, is provided with slightly smaller cross-sectional dimensions so that, when the prosthesis shaft is pushed into the space formed by the rasp, the surface areas in question displace bone substance.

BRIEF DESCRIPTION OF THE DRAWINGS

The invention is explained in more detail below with reference to the drawing, in which.

DETAILED DESCRIPTION OF THE INVENTION

Figure 1:
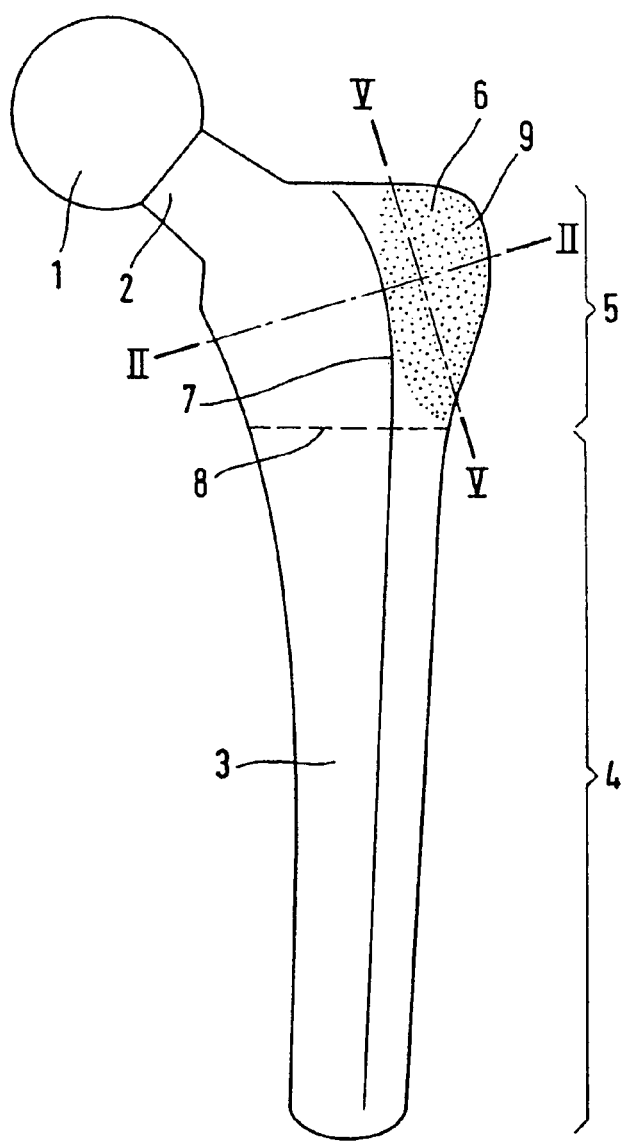
FIG. 1 shows a ventral view of a femoral hip-joint prosthesis.

The hip prosthesis according to FIG. 1 comprises a joint head 1, and a neck 2 which has a shaft 3. The latter has a diaphyseal portion 4 to be anchored in the diaphysis of the bone, and a metaphyseal portion 5 to be anchored in the metaphysis of the bone. The diaphyseal portion is dimensioned such that it ensures primary anchoring of the shaft in the diaphysis of the femur. The person skilled in the art will see, from looking at FIG. 1, how the prosthesis will lie in the bone, and he or she will therefore also know where the border 8 between the diaphyseal and metaphyseal portions of the prosthesis lies.

Whereas the diaphyseal portion 4 of the shaft can bear on the strong cortical bone of the diaphysis and effect primary anchoring there, the metaphyseal portion lies mainly in the spongy bone tissue of the metaphysis.

Figure 2:
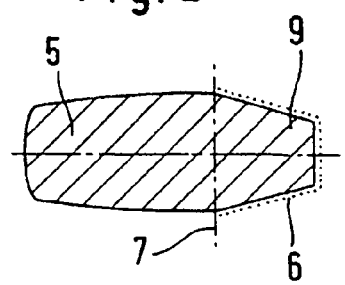
FIG. 2 shows a cross section along line II-II in FIG. 1.
Figure 3:
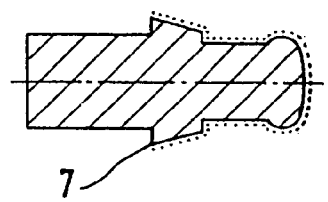
FIGS. 3 and 4 show alternative cross-sectional shapes.

FIG. 2 shows a location 7 having the greatest dimension of the shaft 3 in the AP direction (antero-posterior). The connection of the locations of maximum AP dimension is shown in FIG. 2 as line 7. This extends the entire length of the prosthesis. For the invention, only its extent in the metaphyseal portion 5 is of interest. Laterally from this line, the surface of the shaft in the illustrative embodiment in FIG. 3 is composed exclusively of surface areas in which the surface normal has a component oriented in the lateral direction. This means that it is not possible, by conventional means, to obtain a connection between these surfaces and the bone which is able to take up medially directed prosthesis forces. These forces in fact presuppose a tensile connection between these surface areas and the bone. In the illustrative embodiments according to FIG. 4 or FIG. 5, undercut surface areas are also present laterally from the location or line 7, in which undercut surface areas the surface normal has no component oriented in the lateral direction. However, the laterally directed surface portions also predominate here.

According to the invention, a part 6 of the shaft surface lying in the metaphyseal portion (that is to say above the line 8) and laterally from the line 7 is finished with an osteoinductive substance. This is shown by stippling in the drawing. The finish is preferably contained in a layer of osteoconductive material such as hydroxyapatite. By means of this finish, it is possible to strengthen the connection between the surface areas in question and the bone tissue in such a way that it is able to transmit tensile forces. This means that the tension trajectories in the spongy bone tissue are involved in the take-up of forces and are accordingly not broken down.

In the illustrative embodiment in FIG. 1, the area finished according to the invention includes a projection 9 which lies in the trochanteric area of the metaphysis. Such trochanteric projections are customary for improving the anchoring of the shaft in the bone tissue and for preventing the shaft from turning relative to the bone.

A surface configuration promoting the connection to the bone can also be provided in the other areas of the shaft 3, i.e. medially from the line 7 and distally from the line 8, for example a coating with hydroxyapatite or calcium phosphate. However, it should contain no osteoinductive components there, because otherwise the removal of the prosthesis shaft from the bone in the event of follow-up surgery is made very difficult.

FIG. 2 shows that the projection 13 has a considerable thickness in the antero-posterior direction. Its anterior and posterior surface areas 6 are therefore set back from the central area in which the spongy bone substance is in many cases depleted, and they are situated in a more compact area closer to the cortical bone. Hence, the likelihood of a good connection between the bone surface and the bone substance is further enhanced.

Figure 5:
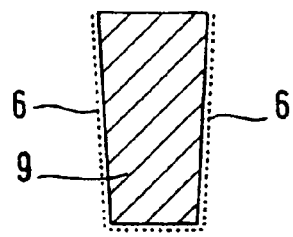
FIG. 5 shows a cross section along line V-V in FIG. 1.
Figure 7:
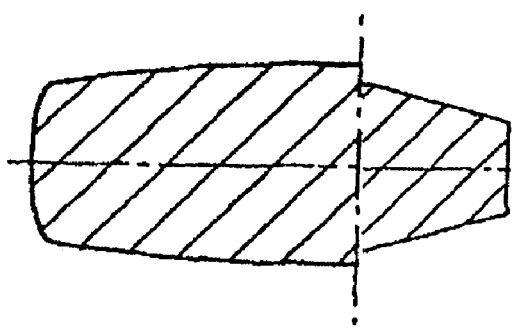
FIG. 7 shows a cross section of a rasp for shaping the receiving space for the shaft of the hip-joint prosthesis.

FIG. 5 shows the cross-sectional shape of the projection 9 in sectional direction V-V, which also corresponds approximately to the direction of insertion. If the hollow space, which has been prepared by means of a rasp (FIG. 7) in order to receive the prosthesis, is slightly smaller than the prosthesis shape, the insertion of this wedge shape into the bone causes a displacement of bone substance and, as a result, an increase in the pressure exerted on the prosthesis surface by the bone substance. In this way too, a rapidly growing and intimate union of the prosthesis surface with the bone is promoted.

Figure 6:
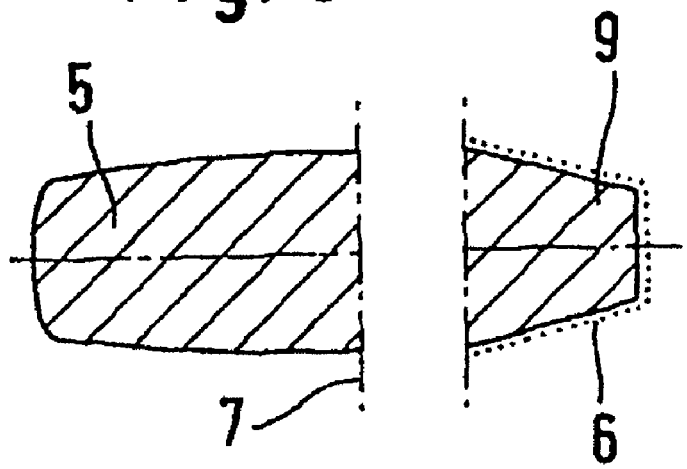
FIG. 6 shows a cross section along line II-II in FIG. 1 with projection 9 detached from shaft 3.

To ensure that the intimate connection between the surface of the trochanteric projection and the bone is not problematic in the event of follow-up surgery, the projection 9 can be detachable from the shaft 3 (FIG. 6). For example, it can be connected to the shaft 3 by means of screws or other connecting means and can be detached from said shaft 3 before the shaft is removed from the bone. The projection can then be more easily released from the bone surrounding it and connected to it.

Figure 4:
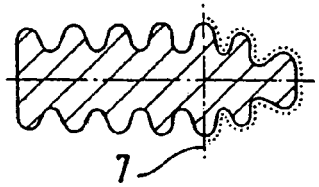

The surface finish according to the invention is not limited to the prosthesis shape shown in FIGS. 1 and 2. Examples of other cross-sectional shapes are shown in FIGS. 3 and 4. Reference number 7 there designates the cross-sectional point of maximum thickness in the AP direction, laterally from which the invention permits an osteoinductive finish of the prosthesis surface.

The invention claimed is:

1. A surgical set containing:
   a hip-joint prosthesis including a shaft which is configured to be inserted into a femur and whose surface is finished with an osteoinductive substance that is provided exclusively on a part of the shaft situated on a lateral side of a boundary delineating a maximum antero-posterior dimension of the shaft cross section in a metaphyseal portion of the shaft and whose surface is free from an osteoinductive substance on a medial side of the boundary, wherein the part of the prosthesis finished with the osteoinductive substance is formed at least partially by a projection extending from the shaft, and
   a rasp for shaping the receiving space for the shaft of the hip-joint prosthesis, wherein the projection is wedge-shaped in an implantation direction and the rasp has a smaller volume in the area of the projection.

2. The surgical set according to claim 1, wherein the osteoinductive substance is formed by a coating on the part of the shaft or is contained in a coating on the part of the shaft.

3. The surgical set according to claim 1 or 2, wherein the osteoinductive substance comprises a bisphosphonate or a bone morphogenic protein.

4. The surgical set according to claim 1 or 2, wherein at least the part of the prosthesis surface containing the osteoinductive substance is porous.

5. The surgical set according to claim 1 or 2, wherein the part of the prosthesis finished with the osteoinductive substance comprises at least two opposite surfaces which point in the ventral and dorsal directions and enclose a spacing in the anteroposterior direction of more than 6 mm.

6. The surgical set according to claim 1 or 2, wherein the projection is configured to be detachable from the shaft.

7. The surgical set according to claim 1 or 2, wherein the part of the prosthesis finished with the osteoinductive substance comprises at least two opposite surfaces which point in the ventral and dorsal directions and enclose a spacing in the anteroposterior direction of more than 9 mm.

* * * * *